United States Patent [19]

Mallonee

[11] Patent Number: 5,955,369
[45] Date of Patent: Sep. 21, 1999

[54] METHOD FOR THE DETERMINATION OF MUTANT RESTRICTION ENZYMES

[75] Inventor: Richard L. Mallonee, Baltimore, Md.

[73] Assignee: Becton, Dickinson and Company, Franklin Lakes, N.J.

[21] Appl. No.: 08/895,074

[22] Filed: Jul. 16, 1997

[51] Int. Cl.⁶ .................................................. C12Q 1/34
[52] U.S. Cl. ............................................ 435/714; 435/18
[58] Field of Search .................................. 435/714, 18, 6

[56] References Cited

U.S. PATENT DOCUMENTS 4,775,619 10/1988 Urdea ........................................ 435/6

OTHER PUBLICATIONS

Yebra, M. J., et al. (1993) Nuc. Acids Res. 21(24), 5797–5798.
Bischofberger, N, et al. (1987) Nuc. Acids Res. 15(2), 709–716.
Estrada, G., et. al. (1996) Mol. Cell. Probes 10, 179–185.
Jsnulaitsi, A. A., et al. (1981) Anal. Biochem. 116, 116–122.

*Primary Examiner*—Charles L. Patterson, Jr.
*Attorney, Agent, or Firm*—Bruce S. Weintraub

[57] ABSTRACT

The present invention is directed to a method for the determination of mutant restriction enzymes which comprises incubating restriction enzymes under non-native conditions with a labeled double stranded oligonucleotide to a solid support to form an enzyme-oligonucleotide complex and detecting the label to determine cleavage of the oligonucleotide by mutant enzymes.

13 Claims, 1 Drawing Sheet

METHOD FOR THE DETERMINATION OF MUTANT RESTRICTION ENZYMES

FIELD OF THE INVENTION

The present invention relates to a method for determining mutant restriction enzymes.

BACKGROUND OF THE INVENTION

Enzymes are highly specific proteins and greatly reduce the activation energy needed in chemical reactions. In addition to its proteinaceous nature, the essence of an enzyme is its catalytic activity. The catalytic activity is characterized by the enzyme's substrates and products, the relationship among which, in turn, define the nature of the reaction catalyzed by the enzyme.

The structures of proteins are determined by genetic information, that is. information that each organism inherits in the form of molecules of deoxyribonucleic acid (DNA). DNA is made up of four types of nucleotides, each of which contains a nitrogenous base, a pentose sugar, deoxyribose, and a phosphate group. The nucleotides differ only in their nitrogenous bases. Oligonucleotides are linear sequences of nucleotides which are joined by phosphodiester bonds. The linear order of nucleotides in a DNA molecule determines the order of amino acids in a protein. The amino acid composition of a protein might be referred to as its zero-order structure and this composition is partially responsible for a protein's net charge and solubility. The amino acids are strung together via amide or peptide bonds and the sequence of amino acids and location of disulfide bridges, if there are any, are termed its primary structure. The primary structure is thus a complete description of the covalent connections of the protein and is at least indirectly responsible for the higher levels of structure and for all properties of the protein, including enzymatic activity. Secondary structure refers to the steric relationship of amino acid residues that are close to one another in the linear sequence. Tertiary structure refers to the steric relationship of amino acid residues that are far apart in the linear sequence. Proteins that contain more than one polypeptide chain display an additional level of structural organization, namely quaternary structure, which refers to the way in which the chains are packed together. A protein's genetic code is characterized by the relationship between the sequence of bases in its DNA and the sequence of its amino acids. Chromosomes, which are threadlike structures consisting of DNA and proteins, carry genes, the units of heredity.

Mutations are inheritable changes in the genetic material, they occur when the position of a nucleotide or of a segment of several nucleotides in the DNA chain is altered, when nucleotides or segments of DNA are added or removed, or when one nucleotide is changed to another. Mutations may result from mistakes in DNA replication or they may be caused by any one of a number of mutagenic agents, which may act by breaking the DNA molecule or by changing the molecular structure of a nucleotide. Since the structure of DNA is responsible for the sequence of amino acids in proteins, mutations may cause changes in the protein for which a segment of DNA codes.

Mutations are not necessarily deleterious and, in fact, there are many reasons for wanting to mutate a gene. Classically, mutagenesis has been used to understand basic processes of genes and gene expression. The identification of genes in pathways, determinations with regard to control of genes, as well as gene mapping have all benefited from mutagenic methods. Recently, recombinant protein expression has made use of newer molecular techniques for mutagenesis. Mutant genes may be generated randomly using chemicals, UV irradiation, polymerase chain reaction (PCR) or by using specifically altered bacterial strains known as mutators. Mutations may also be made at predesignated places by site directed mutagenesis and with PCR.

With gene expression in mind, the goal of mutating a gene is generally to obtain an enzyme which has a desired characteristic the native enzyme lacks. It would be most advantageous to be able to synthesize enzymes or to change individual amino acid residues at will in order to obtain enzymes having specific features imparted to them which, in turn, would give those enzymes greater commercial value. Some examples of such desirable traits would include, but would not be limited to, creation of enzymes having (a) heat stability; (b) increased activity at elevated temperatures; (c) stability or increased activity in a narrow or wide pH range; (d) increased or decreased expression levels; (e) improved solubility; (f) increased binding affinities; (g) recognition of different or modified sequence or receptor sites and (h) exhibition of heterobifunctional activity (ability to work two different ways possibly at the same time).

Endonucleases are enzymes that catalyze breaks in DNA strands at relatively specific sites in specific nucleotide groups. Such restriction endonucleases, or restriction enzymes, provide a means for reproducibly cutting up a molecule into recognizable pieces. A good example of the important role played by restriction enzymes, and the potential commercial impact of their successful synthesis, is illustrated in Strand Displacement Amplification (SDA) developed by G. Terrance Walker, Melinda S. Fraiser, James L. Schram, Michael C. Little, James G. Nadeau and Douglas P. Malinowski, *NucleicAcid Research* 1992, Vol. 20, No. 7, 1691–1696. SDA is an isothermal, in vitro nucleic acid amplification technique based upon the ability of HincII to nick the unmodified strand of a hemiphosphorothioate form of its recognition site, and the ability of exonuclease deficient klenow (exo$^-$ klenow) to extend the 3'-end at the nick and displace the downstream DNA strand. Exponential amplification results from coupling sense and antisense reactions in which strands displaced from a sense reaction serve as targets for an antisense reaction and vice versa. In the original design (G. T. Walker, M. C. Little, J. G. Nadeau and D. D. Shank 1992 *Proc. Natl. Acad. Sci* 89, 392–396), the target DNA sample is first cleaved with a restriction enzyme(s) in order to generate a double-stranded target fragment with defined 5' and 3'-ends that can then undergo SDA. Newer target generation schemes eliminate the requirement for restriction enzyme cleavage of the target sample prior to amplification. The methods exploit the strand displacement activity of exo$^-$ klenow to generate target DNA copies with defined 5' and 3'-ends. The target generation processes occur at a single temperature, after initial heat denaturation of the double-stranded DNA. Target copies generated by these processes are then amplified directly by SDA. The target generation processes can also be applied to techniques separate from SDA as a means of conveniently producing double-stranded fragments with 5' and 3'-sequences modified as desired. It would be most advantageous to be able to perform SDA at higher temperatures as such performance would result in increased specificity, decreased background and improved amplification.

Enzyme activity has been shown to be influenced by many factors, including temperature, pH, substrate and buffer. And, while proteins are known to be intrinsically unstable against heat, the temperature range of thermal stability and the rate of thermal inactivation are very different for different enzymes. Similarly, optimum pH range for a given enzyme's activity varies greatly between different enzymes and may also be dependent upon temperature. Choice and concentration of substrate are of significant importance when trying to determine rate of catalysis since different substrates are converted at different rates. Additionally, rate of catalysis may be impacted by the type of buffer selected.

Enzymatic activity has also been known to be influenced by inhibitors and activators, which are commonly known as "effectors". For example, activator-type effectors may have to be added to an assay mixture to achieve maximum activity whereas inhibitor-type effectors may be present either in the sample or in the reagents or may arise during the reaction in the case of product inhibition. And, while most enzyme-catalyzed reactions show an initial velocity proportional to concentration of enzyme, there are some instances where the relationship does not hold true, as may be the case where small amounts of an enzyme inhibitor is present.

Immunochemical assays generally fall into one of two classifications. In the competitive assay, a limited quantity of binding material is contacted with a solution containing the analyte and a known concentration of a labeled analyte. The labeled and unlabeled analyte compounds compete for the binding sites on the binding material. By reference to a calibration curve, the amount of labeled analyte bound to the binding material can be correlated with the concentration of the analyte in the test solution. A second type of immunological assay, the sandwich assay, involves contacting a binding material with a solution containing the analyte to cause the analyte to bind to the binding material. This complex is then contacted with a solution of a labeled binding material, generally an antibody, which reacts with the bound analyte. The amount of bound labeled binding material is directly proportional to the amount of bound analyte. The sandwich-type assay is generally limited to antigens large enough to accommodate binding of two antibodies simultaneously, one of them being labeled with the marker enzyme. Enzyme-labeled antibodies may be used for the non-radioactive detection of many other classes of biomolecules, such as specific DNA sequences, using DNA-oligonucleotide hybrid formation as the specific recognition principle or carbohydrate residues of glycoproptein, using carbohydrate-lectin binding.

Enzymes to be used in substrate assays have to fulfill a number of quality criteria concerning: (a) specificity, which is the absence of side activities towards other substrates which may be present in the sample or assay mixture; (b) purity, which is the absence of contaminating activities or other contaminants interfering with the analytical and detection systems, not necessarily purity with respect to the absence of other inactive proteins; (c) stability of the test mixture during the assay reaction as well as on long-term storage: (d) kinetic properties: (e) pH optimum; (f) solubility and surface properties which refers to the absence of interference by adsorption or aggregation effects; and (g) cost.

In enzyme immunoassays, enzymes are used as markers for the detection of antibody or hapten-antigen interactions and thus compete with other labeling principles, such as radioisotopes or physicochemical labels. Measurements based on immune reactions have become increasingly popular for determination of high (e.g. catalytically inactive proteins) as well as low molecular weight substances. Conjugates of the marker enzyme with an antibody or hapten may be synthesized by chemical coupling with several bifunctional reagents according to the nature of the reactive groups on the enzyme. Compared to radioimmunoassays, the use of enzymes as labels has the advantage that contact with radioactive materials is avoided, the label may be easily detected with commonly available laboratory equipment and the reagents have a much longer shelf-life.

In each assay method, the unbound labeled material has to be separated from the bound labeled material. A widely used technique for such separation is to immobilize one of the reactants. For instance, an antibody may be adsorbed onto a solid support such as a test tube wall. After labeled material and analyte become bound to the immobilized antibody, the solid support is rinsed free of unbound labeled material.

Most enzyme engineering has been carried out by site-directed mutagenesis following extensive and detailed structural characterization of the enzyme. In nearly all cases this requires a high-resolution three-dimensional structure determined by X-ray crystallography. Mutagenesis of enzymes of unknown chemical structure has been accomplished, by necessity, via random processes. Rellos and Robert K. Scopes, *Protein Expression and Purification* 1994, Vol. 5, 270–277, describe the creation of random mutagens of *Zymomonas mobilis* alcohol dehydrogenase-2 using polymerase chain reaction techniques. Genetic engineering methods have allowed the production of large quantities of known enzymes and have also enabled the utilization of site-directed mutagenesis.

These processes require selection procedures that must screen thousands of mutants for the desired property. What the art lacks is a relatively simple selection procedure to enable the successful screening of large numbers of mutant enzymes. The method of the present invention recognizes the commercial value associated with enzymatic engineering and provides a novel method to successfully screen for desired mutants. According to the present invention, enzymatic mutagenesis is effected randomly, that is via PCR, chemical or mutator strain. From such treatments, a library of mutations is generated from which the desired mutation must be sorted from the wild type and other types of unwanted mutants. Thus, the gene must be phenotypically expressed so that it may be identified. Without such phenotypic expression, mutations may only be determined through sequencing. The particular phenotype sought will be expressed by the ability of a specific enzyme to cleave an oligonucleotide under non-native conditions, that is, those conditions not normally encountered in nature.

SUMMARY OF THE INVENTION

The present invention discloses a method for the determination of mutant restriction enzymes comprising incubating restriction enzymes under non-native conditions with a labeled double stranded oligonucleotide encoding one or more restriction sites of interest to a solid support to form an enzyme-oligonucleotide complex; washing the complex and detecting the label to determine cleavage of the oligonucleotide.

DETAILED DESCRIPTION OF THE INVENTION

Figure 1:
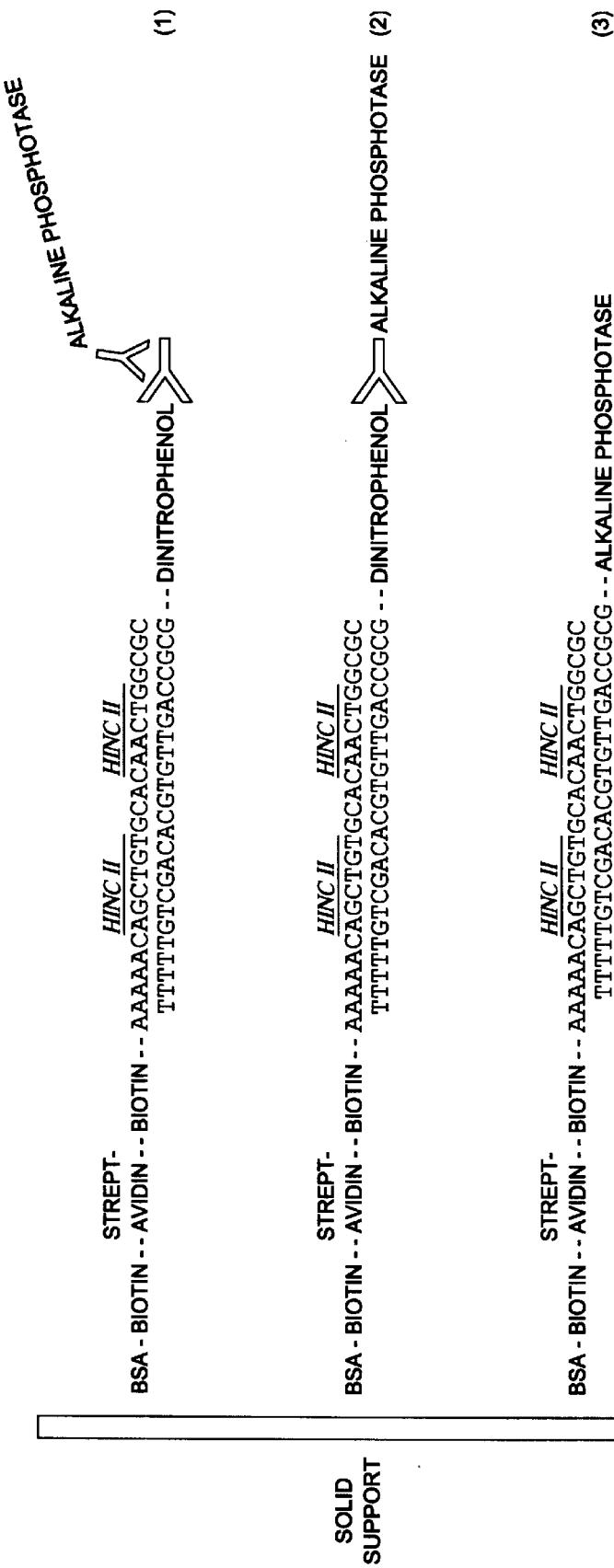
FIG. 1 is a plan view of the assay of the invention.

The present invention is directed to a method for the determination of mutant heat restriction enzymes which comprises incubating a restriction enzyme at a temperature ranging from about 42° C. to about 60° C. with a labeled double stranded oligonucleotide encoding one or more restriction sites to a solid support to form an enzyme-oligonucleotide complex; washing the complex and detecting the label to determine cleavage of the oligonucleotide.

The present invention is also directed to a method for screening bacterial colonies for the detection of mutant restriction enzymes which comprises incubating restriction enzymes under non-native conditions with a labeled double stranded oligonucleotide encoding one or more restriction sites of interest to a solid support to form an enzyme-oligonucleotide complex; washing the complex and detecting the label to determine cleavage of the oligonucleotide by the mutant enzymes.

The method of the present invention may be qualitative. quantitative or semi-quantitative and may generate a calorimetric or fluorometric signal.

With reference to FIG. 1, a double stranded oligonucleotide encoding one or more restriction sites of interest is bound to a solid support. The linkage to the solid support is shown through biotin and streptavadin, but other similar complexes, which would be apparent to a skilled artisan, may also be used. A double stranded oligonucleotide having a biotin attached at one 3'-end and another ligand, in this instance dinitrophenol (DNP) at the other 3' end, is added to the complex. In FIG. 1 (1), the DNP is detected using an anti-DNP antibody and alkaline phosphatase conjugate. In FIG. 1 (2), the DNP is detected directly with an anti-DNP conjugated antibody. In FIG. 1 (3), the oligonucleotide is conjugated with alkaline phosphatase eliminating the need for antibodies.

The restriction enzyme of interest, in this case HincII is allowed to incubate with this final complex under "non-native" conditions. In this particular instance, the assay is carried out by incubating at elevated temperatures to screen for heat stable mutants of the native enzyme.

After this "cutting" step, the plate is washed and the DNP is detected, using a primary antibody and a secondary conjugate, an antibody conjugate, or directly, if a conjugated oligonucleotide is available. After substrate is added, the absence of signal indicates the restriction enzyme has cleaved the double stranded oligonucleotide correctly. under the "non-native" conditions, removing the DNP group. The interpretation of this result is that the enzyme has worked at the elevated temperature and is likely to be a heat stable mutant of the native protein.

It will be readily apparent to a skilled individual that the assay of this invention may incorporate the ELISA (Enzyme Linked Immunoassay) or membrane-type format and may, therefore, utilize any antibody conjugate. which includes, but is not limited to:

(a) Alkaline phosphatase which can be used with one of the following substrates: 5-bromo4-chloro-3-indoyl phosphate/nitro blue tetrazolium (BCIP/NBT); SIGMA (Sigma Chemical Company) Fast Red TR/Naphthol AS-MX; and p-nitrophenyl phosphase (pNPP);

(b) Horseradish peroxidase which can be used with one of the following substrates: 2,2'-azino-bis(3-ethylbcnzthiasoline-6-sulfonic acid)(ABTS); o-phenylenediamine (OPD); 3,3',5,5'-tetramethylbenzidine (TMB), o-dianisidine, 5-aminosalicylic acid (5AS); 3,3'-diaminobenzidine (DAB), 3-amino-9-ethylcarbazole (AEC); and 4-chloro-1-naphthol (4CIN); and (c) Flurocein isothiocyanate and tetramethyl rhodanine isothiocyanate for use with a fluorometer.

The following examples arc for demonstrative purposes and are not intended to in any way limit the present invention.

EXAMPLE 1

A microtiter plate (opaque white) was coated with a bovine serum albumin (BSA) biotin coating solution at 7.5 $\mu$g/mL. 110 $\mu$L of biotin BSA was allowed to incubate for at least two but not more than eight hours at room temperature (i.e., a temperature ranging from about 15° C. to about 30° C.). The wells were rinsed twice with 375 $\mu$L of phosphatc buffered saline (PBS). 110 $\mu$L of streptavadin, which was coated on the plate in two concentrations of 6.35 ng/mL and 3.12 ng/mL, and 0.05% cascin acid hydrolysate solution were applied to the plate and allowed to incubate for 18 to 24 hours at room temperature. The labeled double stranded oligonucleotide was coated at 100 pM and 10 nM respectively, with the above streptavadin concentrations. Native restriction enzyme HincII, (purchased from New England Biolabs) was serially diluted (two fold) from 200 units (manufacturer's value) to 0.195 units as follows: 200, 100, 50, 25, 12.5, 6.25, 3.125, 1.56, 0.78, 0.39 and 0.195. Dilutions were carried out in 1X NEBuffer 3 (New England Biolabs—manufacturer's buffer). (50 mM Tris-HCl (Tris [hydroxymethyl] aminomethane hydrochloride), 10 mM $MgCl_2$, 100 mM NaCl, 1 mM DTT, pH 7.9).

To perform the assay, dilutions were made so that the unit values above are contained in 100 $\mu$L. 100 $\mu$L of each dilution was placed in the microtiter wells and allowed to incubate at a temperature of 37° C. for four hours. Plates were washed with 1 PBS (Phosphate Buffered Saline= working solution, pH~7.3; 137 mM NaCl, 2.7 mM KCl; 4.3 mM $Na_2HPO_4$+7 $H_2O$; 1.4 mM $KH_2PO_4$). To develop the plate, wells were washed with 375 $\mu$L of PBS three times. To each well, 100 $\mu$L of rabbit anti-DNP polyclonal antibody (Sigma Chemical Company) were added at 1:5000, diluted in 1% BSA, 0.05% (v/w) Tween 20 (Polyoxyethylenesorbitan monolaurate from Sigma Chemical Company) in PBS. The plates were incubated, shaking, for one hour at room temperature. The wells were washed with 375 $\mu$L of PBS three times. To each well, 100 $\mu$L of anti-Rabbit alkaline phosphatase conjugate diluted (1:5000) in 1% BSA/0.5% Tween PBS was added. The plates were again incubated, shaking, for one hour at room temperature. The wells were washed with 375$\mu$L of PBS three times. Finally, 100 $\mu$L of Lumi-Phos 530 (Lumigen) (Lumi-Phos 530 contains 4-methoxy-4-(3-phosphatephenyl)spiro[1,2-dioxetane 3,2'-adamantane], disodium salt and fluorescent enhancers for the chemiluminescent detection of alkaline phosphatase) was added to the wells and the plate was incubated for 30 minutes at 37° C. The plates were then read in a luminometer.

With increasing HincII concentration, there was decreasing relative light unit (RLU) signal indicating the oligonucleotide had been cleaved and the portion containing the DNP group had been removed in the wash step.

Presumptive mutant HincII enzymes were screened similarly, using bacterial cell lysates which were added to the wells with the proper buffer conditions. In this case, the enzyme was allowed to incubate at a temperature ranging from about 55° C. to about 60° C. to screen for heat stable mutants. As described above, after this "cutting" step, the plate was washed and the DNP was detected. Absence of signal indicated the restriction enzyme had cleaved the double stranded oligonucleotide. A negative control which does not contain HincII was also included.

Illustrative examples of solid supports envisioned as useful in this invention include, but are not limited to the following:

Membrane type supports—Biodyne A, Biodyne B (Pall Corporation) Imobilon P (Millipore Corporation)

Magnetic Beads—Dynabeads (biomagnetic separation; Dynal, Inc.)

Latex Beads—(Bangs Laboratory, Inc.; Seradyne, Inc.)

All oligonucleotides were synthesized with the label on the 3'-end using "Biotin-On" and "DNP-On" CPG (Controlled Pore Glass—Clontech Laboratories, Inc.). Oligonucleotides were then purified by HPLC (High Performance Liquid Chromatography) on a Brownlee Octyl 20 $C_8$ Reverse Phase Column (Applied Biosystems Inc.). Peak fractions were combined and oligonucleotides were desalted on SepPak Vac RC cartridge (Waters Corporation). Eluent was concentrated in a SpeedVac (Savant Instrument, Inc.). Pellets were resuspended in 1 mL of deionized $H_2O$. The oligonucleotides were mixed in equal molar amounts and allowed to anneal, by first heating to 95° C. then slow cooled to room temperature. To check annealing efficiencies, oligonucleotides were run on a 20% acrylamide Tris Borate, EDTA (TBE) gel [90 mM Tris-Borate, 2 mM EDTA (Disodium Ethylenediaminetetra Acetate)]. In addition, the double stranded oligonucleotides were digested with HincII. Migration shift of fragments occurred. The linkage to the solid support is shown through biotin and streptavidin, but any hapten plus antibody complex could be utilized in the present invention. A double stranded oligonucleotide having a biotin attached at one 3'-end and another ligand, in this instance dinitrophenol (DNP) at the other 3' end, was added to the complex. In FIG. 1 (1), the DNP was detected using an anti-DNP antibody and alkaline phosphatase conjugate. In FIG. 1 (2), the DNP was detected directly with an anti-DNP conjugated antibody. In FIG. 1 (3), the oligonucleotide was conjugated with alkaline phosphatase eliminating the need for antibodies.

The alkaline phosphastase-oligonucleotide conjugate was prepared according to the following scheme:

Oligonucleotide Derivatization: The synthetic oligonucleotide was synthesized with the last base addition (5' end) being an aliphatic primary amine by addition of AminoLink 2 (Amino-Modifier C6 Trifluoroacetyl) (ABI). Purification was accomplished by anion exchange chromatography using an ammonium chloride gradient in the presence of Tris-Cl, pH 8.0. The purified oligonucleotide was derivatized with SPDP (N-Succinimidyl 3-(2-pyridyldithio)propionate) (Pierce Chemical Company) in the presence of potassium phosphate, pH 7.2. SPDP is a heterobifunctional crosslinker containing one H-hydroxysuccinimide (NHS) residue and one pyridyl disulfide residue. The NHS residue reacted with the primary amine present on the 5'-end of the oligonucleotide to form an amide bond. The derivatized oligonucleotide was purified using a disposable G-25 Sephadex (Pharmacia Biotech, Inc.) column.

Alkaline Phosphatase Derivatization: The alkaline phosphatase was derivatized with SMPB (Succinimidyl 4-(p-malcimidophenyl) butyrate) (Pierce Chemical Company) crosslinker. SMPB is a heterobifinctional crosslinker containing one H-hydroxysuccinimide (NHS) residue and one malcimide residue. The NHS-ester reacted with the amine groups present on the alkaline phosphatase, to form an amide bond. The reaction was done in the presence of potassium phosphate, pH 7.5. The derivatized alkaline phosphatase was purified by size exclusion chromatography using a G-25 Sephadcx column.

Conjugation: The alkaline phosphastase-oligonucleotide conjugate was formed by reacting the maleimide moieties of the derivatized alkaline phosphastase with the free sulfides (from SPDP) on the derivatized oligonucleotide. The reaction was done in the presence of potassium phosphate, pH 7.5. The alkaline phosphastase-oligonucleotide conjugate was purified by anion exchange chromatography using a DEAE HR (Diethylaminoethyl, High Resolution) 15 low pressure chromatography column.

The conjugate was stored in a Tris-Cl, NaCl buffer, pH 7.5, containing salmon sperm DNA and sodium azide.

It will be apparent to a skilled individual that in practicing the present invention, any restriction enzyme may be utilized. Illustrative examples of such enzymes include, but are not limited to, Aft II, Agel, BamHI, BspE I, Dra I, EcoR V, Hind III, Nco I, Pst I, Sma I, Xba I.

EXAMPLE 2

A microtiter plate is prepared as in Example 1 but the enzyme dilutions are made in buffers over a pH range of 5.0 to 6.8.

EXAMPLE 3

A microtiter plate is prepared as in Example 1 but the enzyme dilutions arc made in buffers over a pH range of 8.0 to 10.0.

EXAMPLE 4

A microtiter plate is prepared as in Example 1 but the enzyme dilutions are made in buffers which have $MgCl_2$ therein in a concentration range of 1 mM to 5 mM.

EXAMPLE 5

A microtiter plate is prepared as in Example 1 but the enzyme dilutions are made in buffers which have $MgCl_2$ therein in a concentration range of 15 mM to 20 mM.

EXAMPLE 6

In this example, large numbers of bacterial colonies are screened for the production of mutant proteins/enzymes. A culture of bacteria carrying the mutated gene of interest is plated out as follows. A nitrocellulose membrane (NC) is prepared as in Example 1 by coating with the same BSA-biotin-streptavadin-biotin-oliognucleotide complex. The NC membrane is then placed on an agar plate containing LB medium (Luria-Bertani medium), antibiotic and isopropylthio-β-D-galactoside (IPTG). A cellulose acetate filter is placed on top of the coated NC membrane. The bacteria, in this example, recombinant E. coli, (this strain harbors a vector containing the trc promoter for expression of HincII and is inducible with IPTG), is spread on the cellulose acetate filter at a dilution to form single colonies. These plates are then incubated at 37° C. for at least 16 hours to allow bacterial colonies to form and grow. The cellulose acetate membrane containing the colonies is removed and retained for positive colony isolation. The NC membrane is removed and developed, using antibodies at dilutions described in Example 1. Membranes are washed five times with PBS. They are then developed with 5-bromo-4-chloro-3-indolyl phosphate/nitro blue tetrazolium (Sigma Fast BCIP/NBT made by Sigma Chemical Company) as a precipitable substrate. A "negative spot" (absence of color) created by a single colony on a background of precipitated color indicates the restriction enzyme being produced has cleaved the double stranded oligonucleotide.

EXAMPLE 7

When alternative (i.e. non-native) buffer conditions are to be tested, a nitrocellulose membrane (NC) is prepared as in Example 1 by coating with the same BSA-biotinstreptavadin-biotin oliognucleotide complex. The NC membrane is then placed on a plate containing a buffered agarose. A cellulose acetate filter containing the previously grown single colonies (grown on LB medium) is placed on top of the NC membrane. Colonies arc allowed to incubate at 37° C. for a period of at least six hours. The cellulose acetate filter is removed and the NC membrane is developed as in Example 4.

I claim:

1. A method for screening bacterial colonies capable of expressing mutant restriction enzymes of interest, for production of said mutant restriction enzymes, comprising:

a) incubating said bacterial colonies, under desired conditions other than those which are optimal for nonmutant native proteins, with a labeled double stranded oligonucleotide containing one or more restriction sites recognizable and cleavable by mutant restriction enzymes produced by the bacterial colony or colonies, wherein said labeled oligonucleotide is bound to a solid support;

b) forming an enzyme-oligonucleotide complex;

c) washing said complex; and d) detecting the absence or decrease in label wherein said absence or decrease in label signal indicates cleavage of said oligonucleotide by said mutant restriction enzymes under said desired conditions, in order to detect the production of said mutant restriction enzymes by said absence or decrease in label signal.

2. The method according to claim 1 wherein said label is detected with an antibody conjugate.

3. The method according to claim 1 wherein said label is detected with a primary antibody and a secondary conjugate.

4. The method according to claim 1 wherein said oligonucleotide is conjugated and said label is detected directly thereon.

5. The method according to claim 1 wherein said oligonucleotide is labeled with dinitrophenol.

6. The method according to claim 5 wherein said label is detected with an antidinitrophenol antibody and alkaline phosphatase conjugate.

7. The method according to claim 5 wherein said label is detected with an antidinitrophenol conjugated antibody.

8. The method according to claim 5 wherein said oligonucleotide is conjugated with alkaline phosphatase.

9. The method of claim 1 wherein said bacterial colonies and said labeled double stranded oligonucleotide are incubated at a temperature ranging from about 42° C. to about 60° C.

10. The method according to claim 1 wherein said desired condition comprises incubating said bacterial colonies and oligonucleotide in a buffer having a pH ranging from about 5.0 to about 6.8 to determine pH mutants of said enzymes.

11. The method according to claim 1 wherein said desired condition comprises incubating said bacterial colonies and oligonucleotide in a buffer having a pH ranging from about 8.0 to about 10.0 to determine pH mutants of said enzymes.

12. The method according to claim 1 wherein desired condition comprises incubating said bacterial colonies and oligonucleotide in a buffer having a magnesium concentration in an amount ranging from about 1 mM to about 5 mM to determine mutants of said enzymes wherein said mutants have improved binding affinities and activity.

13. The method according to claim 1 wherein said desired condition comprises incubating said bacterial colonies and oligonucleotide in a buffer having a magnesium concentration in an amount ranging from about 15 mM to about 20 mM to determine mutants of said enzymes wherein said mutants have improved binding affinities and activity.

* * * * *